United States Patent [19]

Saudagar

[11] Patent Number: 4,555,242
[45] Date of Patent: Nov. 26, 1985

[54] URINARY DRAINAGE APPLIANCE

[76] Inventor: Abdul S. Saudagar, 12 Eastshore, Irvine, Calif. 92714

[21] Appl. No.: 572,687

[22] Filed: Jan. 19, 1984

[51] Int. Cl.$^4$ ............................................. A61M 25/00
[52] U.S. Cl. ....................................... 604/96; 128/344
[58] Field of Search .................................. 604/95–104, 604/271, 327, 328, 332, 335; 128/1 R, 151, 152, 344, DIG. 25

[56] References Cited

U.S. PATENT DOCUMENTS

| 2,457,244 | 12/1948 | Lamson | 128/246 |
| 3,447,533 | 6/1969 | Spicer | 128/1 |
| 3,642,005 | 2/1972 | McGinnis | 128/351 |
| 3,841,304 | 10/1974 | Jones | 128/1 R |
| 4,241,735 | 12/1980 | Chernov | 128/344 |
| 4,340,046 | 7/1982 | Cox | 604/96 |
| 4,351,342 | 9/1982 | Wiita et al. | 128/344 |

FOREIGN PATENT DOCUMENTS 676943  6/1929  France .

OTHER PUBLICATIONS

Leaflet—Dow Corning—"New Product Information, SILASTIC Q7–2213 Medical Grade Dispersion".

Primary Examiner—P. E. Konopka
Attorney, Agent, or Firm—Klein & Szekeres

[57] ABSTRACT

An appliance for draining bodily wastes from the natural bladder of a patient, or from an artificial bladder, through a surgically-created stoma, includes a tube insertable into the bladder through the stoma, and an inflatable balloon enclosing a substantial portion of the length of the tube. The balloon has a corrugated tubular portion terminating in a bulbous tip portion. The tip is located at the end of the tube to be received in the bladder, while the corrugated portion extends along the length of the tube which is received in the passage from the bladder created by the stoma. An inflation fluid is introduced into the interior of the balloon through an inlet in an external retainer plug and through fluid passages and ports in the tube. The balloon has an expandable wall which is thicker in the tip portion than in the corrugated portion, so that the corrugated portion can be substantially fully inflated before the tip portion inflates. The tip portion, when inflated, forms a donut-shaped cushion around the end of the tube in the bladder, while the corrugated portion inflates to provide a fluid-tight seal around the tube.

19 Claims, 6 Drawing Figures

URINARY DRAINAGE APPLIANCE

BACKGROUND OF THE INVENTION

This invention relates generally to the field of surgical appliances for draining bodily wastes through a surgically-created bodily opening. In particular, the invention relates to an appliance for draining a person's natural bladder, or a surgically-created artificial bladder, through an abdominal stoma.

A person may, because of injury, malignancy, birth defects, or nerve damage, suffer the loss of the bladder or loss or impairment of the bladder function. To provide urinary drainage for such a person, a urinary ostomy, or urinary diversion, must be performed, whereby an artificial bodily opening is provided for the outflow of urine.

A common urinary ostomy procedure is that which is frequently termed an "ileal conduit." This procedure, which is used when the bladder is removed or bypassed, involves the separation of a segment of the lower ileum, about six inches in length, with the blood supply intact. One end of the ileal segment is sutured shut; the other end is brought through the abdominal wall (usually in the lower right quadrant) to form an opening, or stoma, to the outside of the body. The ileal segment now forms an "ileal bladder", and the ureters, which convey urine from the kidneys to the bladder, are connected to the ileal bladder. The stoma thus forms a urinary passage from the ileal bladder to the outside of the body.

Another surgical procedure which is frequently performed is known as a cystostomy or a vesicostomy. In this procedure, an opening is made into the body and into the bladder, allowing the bladder to drain directly through a stoma, rather than through the urinary sphincter and the urethra. Still another procedure, known as a ureterostomy, involves detaching the ureters from the bladder and draining them into one or two abdominal stomas.

All of the above procedures result in a loss of voluntary control of the passage of urine. Therefore, drainage and collection devices must be used to contain the drained urine until it can be disposed of. Typical prior art devices include a tube, one end of which is inserted into the bladder (natural or artificial) through the stoma, with the other end draining into a removable collection device, such as a bag or a pouch. Frequently, an expandable elastic balloon (also known as an inflatable "cuff") surrounds the tube near its inner end. When inflated, the balloon forms a fluid seal around the tube at the opening of the bladder into the stoma, and further secures the tube against dislodgment. An early example of such a device is disclosed in French patent no. 676,943; a more modern version of this concept is embodied in the device which is well-known to medical practitioners as the Foley catheter.

These prior art devices have several drawbacks. For example, it is difficult with these devices to obtain a good, fluid-tight seal around the drainage tube within the bladder and within the stoma. This is largely a result of the uneven surface of the tissues involved, and the inability of the prior art devices to engage such tissues in a secure sealing contact, while being sufficiently gentle to avoid discomfort. As a result, leakage of urine around the tube is frequently a problem, leading to unpleasant odor, skin irritation, and, possibly, infection.

Another problem with prior art devices is that the inner tissues of the bladder can frequently come into contact with the inner end of the drainage tube. These tissues can, as a result, become painfully irritated. In the case of a natural bladder, encrustations and painful spasms can also result.

Still another problem with such devices is that they must frequently be secured to the outside of the body by adhesive tape, which can cause skin irritation, leading to possible infection. Yet another problem is that the attachment of the collection bag or pouch frequently requires the surgical formation of a "rosette" at the skin site around the stoma, thereby adding complexity and time to the surgical procedure involved.

All of these drawbacks make the prior art devices inconvenient, and frequently uncomfortable, to wear. Moreover, the need for frequent cleaning of the drainage device and the drainage site make removal of the device mandatory every two or three weeks, thereby contributing to the inconvenience of their use.

It will thus be appreciated that there is a need for a drainage device or appliance which overcomes the aforementioned drawbacks, and which therefore provides a conveniently used, comfortably worn means of voiding urinary wastes through a stoma, and which can be worn for extended periods of time without undue concern for leakage, irritation, or infection.

SUMMARY OF THE INVENTION

Briefly, the present invention comprises a flexible drainage tube, a major portion of the length of which is enclosed by an inflatable balloon having a ribbed, or corrugated portion along its length for sealing engagement with the interior of the stoma through which the tube is inserted into the bladder (whether natural or artificial). The portion of the balloon surrounding the inner end of the tube, which is inserted into the bladder, has an enlarged diameter, bulbous configuration. The wall thickness of the balloon is made lesser along its ribbed portion than at its bulbous end, so that inflation of the balloon occurs in two distinct stages: first, along the ribbed length of the balloon that is situated in the urinary passage formed by the stoma; and second, at the bulbous end situated within the bladder. The bulbous balloon end, when inflated, surrounds the inner end of the drainage tube, and extends slightly beyond it axially, to prevent the tube from coming into contact with the bladder tissues, with the aforementioned consequences.

A retainer plug is provided at the outer end of the tube. The plug has an inner flange to assist in stabilizing the appliance in place and further sealing against leakage, and an outer flange for removable attachment of a collection bag.

Inflation of the balloon is by means of a suitable fluid (gas or liquid) delivered from a syringe or the like through a series of passages formed in the plug and the sidewall of the tube, which passages deliver the fluid to the space between the tube and the balloon.

As will be appreciated more thoroughly from the detailed description which follows, the present invention offers several distinct advantages over the prior art devices. First, the ribbed construction of the balloon provides a firm but gentle sealing engagement with the uneven surface of the tissues lining the stoma, thereby substantially eliminating leakage while maintaining comfort. Second, the bulbous tip of the balloon provides an effective fluid-tight seal around the tube at the opening of the bladder into the urinary passage, thereby further minimizing leakage. The bulbous tip further forms a cushion around the tube end within the bladder to reduce or eliminate any irritating contact between the bladder tissue and the tube, as mentioned above. Third, the two-stage inflation process assures that sufficient inflation occurs along the ribbed section of the balloon to provide the above-mentioned sealing function to a very reliable degree. Fourth, the combination of the retention plug, the ribbed section of the balloon, and the cushion-seal of the bulbous balloon tip all provide very effective stability against displacement of the appliance, both axially and radially, within the urinary passage, thereby minimizing irritation and discomfort. Fifth, the stability of the appliance, its effective sealing function, and the configuration of the retention plug obviate the need for a surgically-created "rosette" at the stoma site, while also eliminating the need for adhesive tape to secure the appliance. Sixth, the overall construction of the appliance, in minimizing both discomfort and leakage, provides for less frequent removal for cleaning and the like.

These and other advantages are provided by a device which is relatively economical to manufacture and simple to install and use, as will be made clear from the detailed description which follows.

DETAILED DESCRIPTION OF A PREFERRED EMBODIMENT

Figure 2:
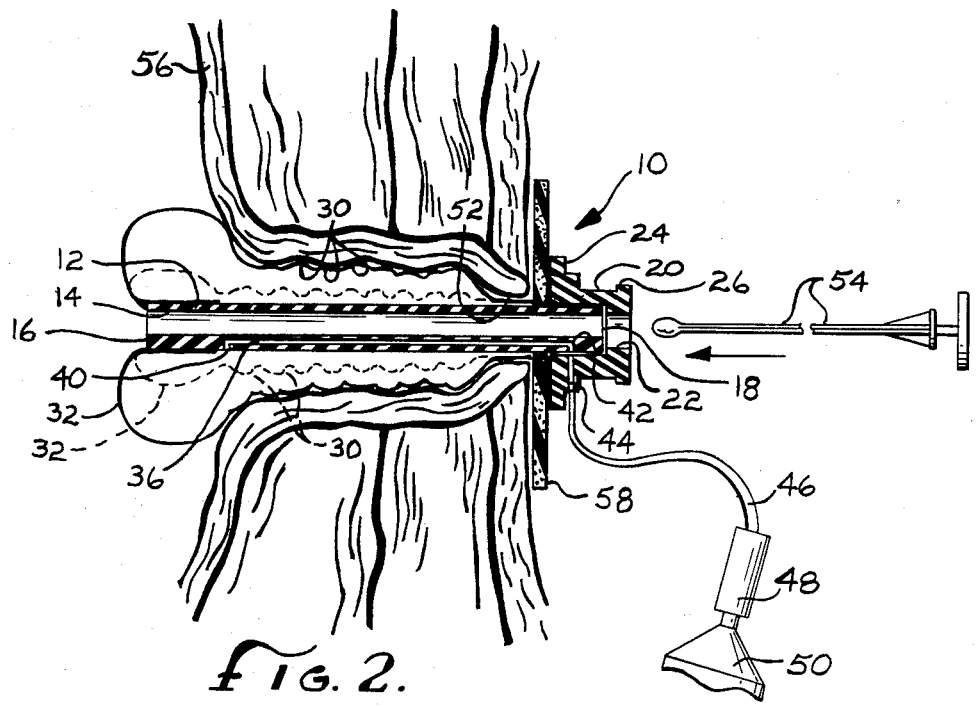
FIG. 2 is a cross-sectional view along line 2—2 of FIG. 1, showing the appliance fitted within a surgically-created stoma.
Figure 1:
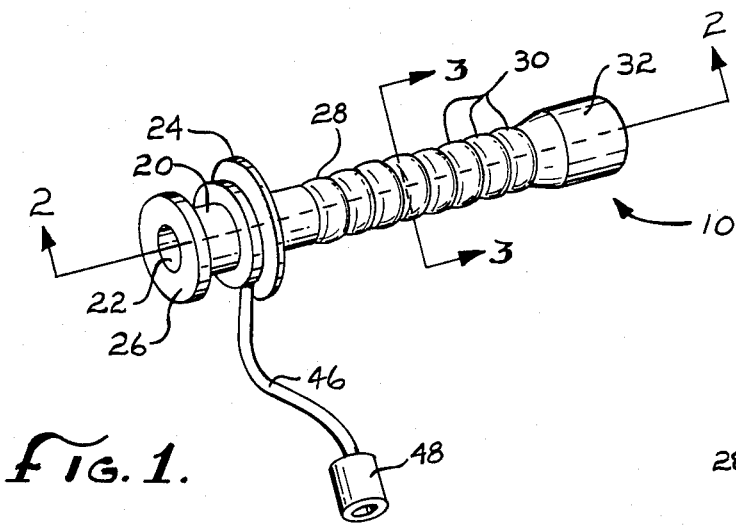
FIG. 1 is a perspective view of a drainage appliance in accordance with a preferred embodiment of the invention.
Figure 3:
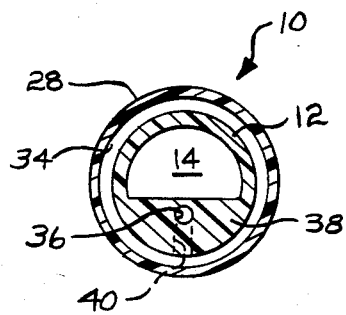
FIG. 3 is a cross-sectional view along line 3—3 of FIG. 1.

A drainage appliance 10, in accordance with a preferred embodiment of the present invention, is illustrated in detail in FIGS. 1, 2, and 3. As best shown in FIG. 2, the appliance 10 comprises a flexible tube or conduit 12 made of a bio-compatible polymer. The tube 12 has an axial bore 14 extending from an inner, or distal end 16 to an outer, or proximal end 18. A retainer plug 20 is securred, as by bonding or threading, to the outer end 18 of the tube 12. The plug 20 has an axial bore 22, which is aligned with the bore 14 of the tube 12, and inner and outer peripheral flanges 24 and 26, respectively, for purposes to be described below.

An inflatable balloon 28 is formed around the tube 12 along a major portion of its length by bonding a corrugated tubular membrane of expandable material to the tube near the latter's inner and outer ends. The process by which the attachment of the membrane is performed will be described in some detail below. At this point, however, it is appropriate to describe the physical characteristics of the balloon 28.

Specifically the ballon 28 is preferably formed of a silicone dispersion or a dimethylsiloxane elastomer dispersion, with physical properties falling within the following approximate ranges when cured:
Tensile Strenth (lbs/in$^2$): 1200–1500
Elongation Percent: 600–900
Tear (lbs/in): 100–200
Durometer, Shore A: 30–80

A suitable material is marketed by Dow Corning Corp., Midland, Mich., under the trademark Silastic ® Q7-2213 Medical Grade Dispersion. Other materials, such as polyvinylchloride (pvc) or polyurethane may also be used.

It can be seen from the drawings that the balloon 28 includes a tubular portion having a plurality of circumferental ribs or corrugations 30. The distal end of the balloon 28 terminates in a somewhat bulbous tip 32. For reasons which will be made clear below, the wall thickness of the balloon 28 at its tip 32 is measurably greater than the thickness throughout the tubular portion.

As best shown in FIG. 3, a space or chamber 34, annular in cross-section, is formed between the conduit 12 and the balloon 28. An axial passage or lumen 36 is provided through an axially-extending thickened sidewall segment 38 (FIG. 3) of the conduit 12. The lumen 36 is separated from, and parallel to, the axial bore 14, and it communicates with the chamber 34 via a first fluid port 40 near the distal end of the conduit 12. A second fluid port 42 near the proximal end of the conduit 12 communicates with a radially-extending fluid inlet 44 in the retainer plug 20. The inlet 44 receives one end of a flexible tube 46, the other end of which communicates with an inflation valve 48. The inflation valve 48 is of a conventional design, of the type in common use for the inflation of catheter cuffs and the like, and therefore there is no need to describe it in detail. It is adapted to receive a syringe 50 from which the balloon 28 will be inflated with a suitable gas or liquid, as will be discussed below.

The use and operation of the appliance 10 is illustrated in FIG. 2. As previously discussed, as a result of surgery, the patient is provided with a stoma 52 in the abdominal wall. The appliance 10 is inserted, in its uninflated state (dotted outline), through the passage which is formed by the stoma. Since the conduit 12 is flexible, a stylet 54 may be inserted into the bore 14 to facilitate insertion. Properly inserted, the distal end 16 of the conduit 12, surrounded by the bulbous tip 32 of the balloon 28, will be situated within the bladder 56 (either the natural bladder or an ileal bladder, as discussed above). The proximal, or outer end 18 of the conduit 12, with the attached retainer plug 20, extends beyond the stoma opening. Thus situated, the inner flange 24 at the distal end of the retainer plug 20 will either rest against the abdominal skin, or as shown, against a removable foam spacer 58 (one or more of which can be selectably installed or removed to achieve proper spacing as the patient's abdomen distends or shrinks due to eating, for example).

The appliance can now be fixed in place by inflating the balloon 28 with a suitable gas or liquid from the syring 50. For a balloon made of a silicone elastomer, as described above, the preferred inflation fluid is a normal saline solution; distilled water may also be used. If the balloon is made of a polyvinylchloride (pvc) or polyurethane film, air can be used for inflation. (It should be noted that the balloon 28 and conduit 12 are preferably made of the same or similar materials.)

In any case, the inflation fluid is delivered, via the valve 48, tube 46, inlet 44, proximal fluid port 42, lumen 36, and distal fluid port 40 into the chamber 34 between the balloon 28 and the conduit 12. Because the wall thickness of the balloon 28 is lesser throughout its tubular portion than at its tip 32, the tubular portion inflates substantially fully before the tip begins to inflate. In this manner, the ribs 30 of the balloon can be expanded to engage, firmly but gently, the uneven inner surface of the urinary passage. When the tubular portion of the balloon 28 is fully expanded in the urinary passage, the bulbous tip begins to expand within the bladder to provide a snug but gentle sealing fit around the entry of the urinary passage within the bladder. As shown in FIG. 2, the expanded tip 32 surrounds the periphery of the distal end 16 of the conduit and forms a generally donut-shaped cushion which extends radially outwardly from the distal end, while also extending axially past it, leaving the opening therein unobstructed.

The above-described balloon structure offers several significant advantages. First, the ribs 30 provide retention of the appliance in place within the urinary passage by firmly, but gently, engaging the irregular surface of the tissues therein. This engagement not only reduces the possibility of axial displacement of the appliance, it also enhances radial stability of the appliance within the urinary passage while also providing an effective seal against leakage through the urinary passage around the appliance. Second, by providing for balloon inflation in two distinct stages (i.e., the tubular ribbed section first, then the bulbous tip), full expansion of the ribbed tubular section is assured. In other words, if, for example, the balloon were of uniform thickness throughout, pressure on the tubular portion of the balloon applied by the tissues of the urinary passage would cause balloon inflation to occur primarily at the tip 32, which is not subjected to such pressures. Thus, full expansion of the ribbed section to provide a firm fit within the urinary passage would be impaired. Finally, the configuration of the tip 32 (i.e., its axial extension beyond the distal end of the conduit and its radial expansion around the opening from the bladder to the urinary passage) provides a firm, but well-cushioned axial retention function, and a fluid-tight seal around the urinary passage opening to prevent leakage. It also very effectively protects the bladder tissues from contact with the conduit 12, thereby minimizing irritation and the possibility of resultant bladder spasms.

With the appliance 10 installed, as described above, it can thus be seen that a comfortable, fluid-tight, and stable (axially and radially) fit can be maintained for prolonged periods of time, up to, perhaps, two or three months, as opposed to the two or three weeks typical with prior art devices. This fit is accomplished without the need for adhesive tape and the like to maintain the apppliance in place, and without the need for surgical creation of a "rosette" at the skin site around the stoma. It can also be appreciated with inner flange 24 of the retention plug, engaging the skin or the spacer 58, enhances the axial stability of the device and its comfort for extended periods of time, while also providing a redundant seal around the stoma opening. In use, of course, a suitable collection device, such as a bag (not shown) can be removably attached, by conventional means, around the outer portion of the retainer plug 20, the axial bore of which forms an outlet for the urine passing therethrough. The outer flange 26 at the proximal end of the plug 20 provides an advantageous attachment site.

Removal of the appliance 10 merely requires deflation of the balloon 28 and withdrawal of the appliance from the stoma.

Figure 4:
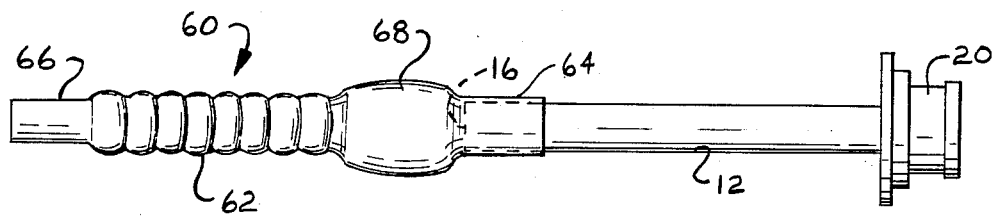
FIGS. 4, 5, and 6 are simplified elevational views showing some of the steps in the process of manufacturing the appliance.
Figure 5:
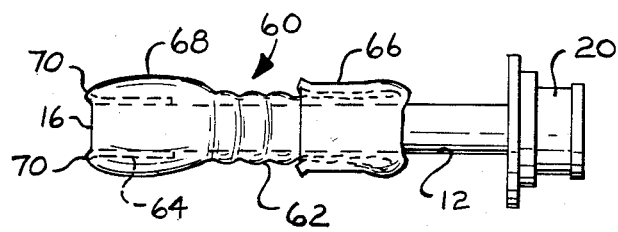
Figure 6:
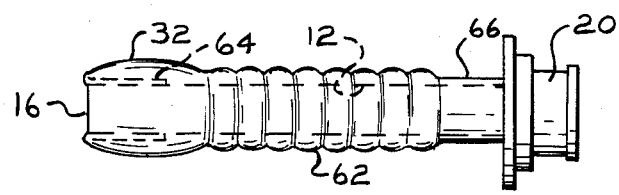

FIGS. 4 through 6 illustrate the steps in the process of forming the balloon 28 around the conduit 12.

First, a generally tubular membrane 60 of suitable material, as discussed above, is provided. The membrane has a ribbed section 62 forming a major portion of its length, with unribbed, tubular first and second end sections 64 and 66, respectively. Adjacent the first end section 64 is an enlarged-diameter section 68 which, as will be shown, will form the bulbous tip 32.

As seen in FIG. 4, the first end 64 of the membrane tube 60 is slipped over the distal end 16 of the conduit 12, and is attached thereto by a suitable adhesive, or by thermal or ultrasonic bonding. Next, the tubular membrane 60 is rolled over the first end 64 and the conduit 12, as shown in FIG. 5, so that the enlarged-diameter section 68 surrounds the distal end 16 of the conduit, extending slightly beyond it, as at 70. Finally, as shown in FIG. 6, the second end 66 of the tubular membrane is attached to the conduit 12 adjacent the retainer plug 20, in a manner like that used to attach the first end 64. Thus, as shown, the enlarged-diameter portion has become the bulbous tip 32, and the ribbed section 62 is properly located along the length of the conduit 12, extending proximally from the tip. This construction provides a good, fluid tight seal at the ends 64 and 66, using a process that is relatively simple and economical to carry out.

It will be appreciated from the foregoing description that the dimensions of the appliance are selected as appropriate for each individual patient. Some dimensions, such as the wall thickness of the balloon, for example, may vary according to the particular materials used.

It will also be appreciated that the appliance is easily adaptable to a wide variety of uses. Thus, although primarily intended for use with ileal bladders and vesicostomies or cystostomies, the appliance, with, perhaps, minor modifications, can be used for colonic bladders, ureterostomies, ileostomies, and some colostomies and nephrostomies. In some of these applications, of course, the appliance must be dimensioned to allow passage of fecal wastes.

The multitude of advantages provided by the invention can now be readily appreciated. As previously mentioned, the unique construction of the balloon, including its ribbed section, bulbous tip, and two-stage inflation, provides for very effective sealing against leakage, good long-term stability against dislodgment and/or displacement, and minimal discomfort, without the need for adhesive tape and the problems associated with its use. The balloon construction and especially the bulbous tip, minimizes irritation of the bladder and urinary passage tissues, thereby reducing the likelihood of painful inflammation, spasms, and infections. The effective sealing and stabilizing functions, enhanced by the retainer plug, make the surgical creation of a "rosette" at the stoma site unnecessary, thereby reducing the time and complexity of the stoma-forming surgery. (Other than obviating the need for a rosette, the surgical procedure used in fitting the present invention is not changed from current practices.) The comfort, stability, and effective sealing allow longer intervals between removal for cleaning the device and the stoma. Moreover, when removal is required, this can be accomplished easily by the patient, who can then quickly and easily clean the appliance and re-insert it. The low profile of the external structure (i.e., the retainer plug) reduces the conspicuousness of the device, even when a bag is worn. In this regard it should be noted that vesicostomy patients, may, during waking hours, simply place a stopper (not shown) in the outlet of the retainer plug, thereby eliminating the need to wear a bag at all times.

The above-noted advantages can significantly reduce the negative psychological impact of wearing the appliance, by making its presence less conspicuous and more comfortable, and by allowing the patient greater freedom of action while reducing fear of malodorous and potentially embarrassing leaks.

It should also be noted that the appliance is made of materials that, while durable and strong, are lightweight and soft or pliable, thereby enhancing the patient's comfort.

It will further be appreciated that these advantages are achieved with a structure that is relatively economical to manufacture and simple to use.

Although a specific preferred embodiment of the invention has been described above and in the drawings, it will be appreciated that, as noted above, modifications may be made to adapt the appliance to a variety of applications. These modifications should be considered within the spirit and scope of the invention, as defined in the claims which follow.

What is claimed is:

1. A device for draining bodily wastes from a natural or artificial bladder in a patient's body through a stoma connected with said bladder by a passage, said device comprising:

conduit means insertable into said bladder through said stoma and said passage, for allowing the passage of bodily wastes from said bladder to the exterior of the body through said stoma, said conduit means having a distal end adapted to be received in said bladder and a proximal end axially spaced from said distal end so as to extend to the exterior of the body through said stoma;

external retention means, attached to said proximal end of said conduit means, for sealing said stoma around said proximal end and forming an outlet for wastes discharged from said proximal end;

an inflatable balloon enclosing the exterior of said conduit means along a substantially portion of its length from said distal end thereof, said balloon having a bulbous tip portion surrounding said distal end and a ribbed portion extending proximally from said tip portion, said balloon and said conduit means defining a space therebetween; and passage means, communicating with said space, for providing a flow path for a fluid into said space to inflate said balloon;

said balloon having a wall which is thicker in said tip portion than in said ribbed portion so as to allow said ribbed portion to be substantially fully inflated before said tip portion is inflated when said ribbed portion is situated in said passage and said tip portion is situated in said bladder.

2. The device of claim 1, wherein said tip portion of said balloon, when inflated, extends axially beyond said distal end of said conduit means.

3. The device of claim 1, wherein said balloon comprises:

a first tubular end section sealingly attached around said distal end of said conduit means;

a second tubular end section rolled over said first tubular end section and sealingly attached around said conduit means adjacent said proximal end thereof;

an enlarged-diameter section overlying said first tubular end section and forming said bulbous tip portion; and;

a corrugated tubular section, extending from said enlarged-diameter section to said second tubular end section, and forming said ribbed portion.

4. The device of claim 1, wherein said conduit means includes a hollow, flexible tube.

5. The device of claim 4, wherein said tube includes an axial bore, and wherein said external retention means comprises:

a retainer plug having a distal end and a proximal end and an axial bore therebetween, said axial bore being aligned with the axial bore of said tube; and a peripheral flange around said distal end of said retainer plug.

6. The device of claim 4, wherein said tube has an axial bore from said distal end to said proximal end thereof, and wherein said passage means comprises:

an axial passage in said tube, separated from, and parallel to, said axial bore, said axial passage having a proximal end and a distal end;

a first fluid port communicating between said distal end of said axial passage and a space defined between the exterior of said tube and the interior of said balloon;

an inflation fluid inlet in said external retention means; and a second fluid port communicating between said proximal end of said axial passage and said inflation fluid inlet.

7. The device of claim 1, wherein said external retention means includes means forming a site for the removable attachment of a receptacle for the capture of bodily wastes flowing through said outlet.

8. A device for draining bodily wastes from a natural or artificial bladder in a patient's body through a stoma connected with said bladder by a passage, said device comprising:

a flexible tube insertable into said bladder through said stoma and said passage, and having a distal end adapted to be received in said bladder, a proximal end axially spaced from said distal end so as to extend to the exterior of the body through said stoma;

external retention means, attached to said proximal end of said tube, for (a) resisting axial displacement of said tube, (b) sealing said stoma around said proximal end, and (c) forming an outlet for the discharge of wastes flowing through said tube;

first inflatable means on said distal end of said tube, which, when inflated, extends radially outwardly from said distal end and axially beyond said distal end, for (a) resisting, with said external retention means, the axial displacement of said tube, (b) providing a fluid-tight seal around said distal end of said tube, and (c) providing a cushion around said distal end substantially to prevent direct contact between said tube and the tissues of said bladder;

second inflatable means, enclosing a substantial portion of the length of said tube extending proximally from said first inflatable means, for providing, when inflated, a substantially fluid-tight seal between said tube and said passage; and passage means in said external retention means and said tube, for providing a flow path for a fluid into said first and second inflatable means for the inflation thereof;

said first and second inflatable means each having an expandable wall, the expandable wall of said first inflatable means being thicker than the expandable wall of said second inflatable means, so that said first inflatable means is permitted to begin inflating only after said second inflatable means is substantially fully inflated when said tube is inserted into said bladder through said stoma and said passage.

9. The device of claim 8, wherein said first and second inflatable means form, respectively, first and second portions of an inflatable balloon, said balloon having an expandable wall with a greater thickness in said first portion that in said second portion, thereby to permit said second poriton to inflate substantially fully before said first portion begins to inflate.

10. The device of claim 9, wherein said first portion of said balloon is a bulbous tip portion, and said second portion has a plurality of circumferential ribs which, when said second portion is inflated, sealingly engage the tissues of said passage.

11. The device of claim 10, wherein said balloon further comprises:
 a first tubular end section sealingly attached around said distal end of said tube;
 a second tubular end section rolled over said first tubular end section and sealingly attached around said tube adjacent said proximal end thereof;
 an enlarged-diameter section overlying said first tubular end section and forming said bulbous tip portion; and
 a corrugated tubular section, extending from said enlarged-diameter section to said second tubular end section, and forming said second portion of said balloon.

12. The device of claim 8, wherein said tube has an axial bore extending from said distal end to said proximal end, and wherein said external retention means comprises:
 a retainer plug having a distal end, a proximal end, and an axial bore therebetween aligned with the axial bore of said tube; and
 a peripheral flange around said distal end of said retainer plug.

13. The device of claim 9, wherein said tube has an axial bore from said distal end to said proximal end thereof for the flow of said wastes from said bladder to the outlet formed by said external retention means, and wherein said passage means comprises:
 an axial passage in said tube, separated from, and parallel to, said axial bore, and having a proximal end and a distal end;
 a first fluid port communicating between said distal end of said axial passage and a space defined between the exterior of said tube and the interior of said balloon;
 an inflation fluid inlet in said external retention means; and
 a second fluid port communicating between said proximal end of said axial passage and said inflation fluid inlet.

14. The device of claim 13, wherein said axial passage is formed in an axially-extending, thickened sidewall segment of said tube.

15. A device for draining bodily wastes from a natural or artificial bladder in a patient's body through a stoma connected with said bladder by a passage, said device comprising:
 a flexible tube, insertable into said bladder through said stoma and said passage, and having a distal end adapted to be received in said bladder, a proximal end axially spaced from said distal end so as to extend to the exterior of the body through said stoma, and an axial bore extending from said distal end to said proximal end;
 a retainer plug attached to said proximal end of said tube and having an axial bore aligned with the axial bore of said tube;
 an inflatable balloon enclosing the exterior of said tube along a substantial portion of its length from the distal end thereof, said balloon having a bulbous tip portion surrounding the periphery of said distal end and a ribbed portion extending proximally from said tip portion, said balloon and said tube defining a space therebetween, said bulbous tip portion being inflatable to form a donut-shaped cushion extending radially outwardly from said distal end and axially beyond said distal end, said ribbed portion being inflatable to form a substantially fluid-tight seal between said tube and said passage, said balloon having an expandable wall which is thicker in said tip portion than in said ribbed portion, thereby allowing said ribbed portion to be substantially fully inflated before said tip portion is inflated when said ribbed portion is situated in said passage and said tip portion is situated in said bladder; and
 passage means, in said retainer plug and said tube, for providing a flow path for a fluid from a fluid source into said space between said balloon and said tube to inflate said balloon.

16. The device of claim 15, wherein said balloon comprises:
 a first tubular end section sealingly attached around said distal end of said tube;
 a second tubular end section rolled over said first tubular end section and sealingly attached around said tube adjacent said proximal end thereof;
 an enlarged-diameter section overlying said first tubular end section, extending from said enlarged-diameter section to said second tubular end section, and forming said ribbed portion.

17. The device of claim 15, wherein said retainer plug has a distal end and a proximal end, and a peripheral flange around said distal end.

18. The device of claim 15, wherein said passage means comprises:
 an axial passage in said tube, separated from, and parallel to, said axial bore, said axial passage having a proximal end and a distal end;
 a first fluid port communicating between said distal end of said axial passage and said space between said balloon and said tube;
 an inflation fluid inlet in said retainer plug; and
 a second fluid port communicating between said proximal end of said axial passage and said inflation fluid inlet.

19. The device of claim 18, wherein said axial passage is formed in an axially-extending, thickened sidewall segment of said tube.

* * * * *